(12) United States Patent
Govyadinov et al.

(10) Patent No.: US 12,599,901 B2
(45) Date of Patent: Apr. 14, 2026

(54) MICROFLUIDIC REACTION CHAMBER WITH A REACTION CHAMBER CIRCUIT

(71) Applicant: HEWLETT-PACKARD DEVELOPMENT COMPANY, L.P., Spring, TX (US)

(72) Inventors: Alexander Govyadinov, Corvallis, OR (US); Hilary Ely, Corvallis, OR (US); Brett E. Dahlgren, Corvallis, OR (US); Si-lam J. Choy, Corvallis, OR (US); Erik Torniainen, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 986 days.

(21) Appl. No.: 17/782,598

(22) PCT Filed: Jan. 21, 2020

(86) PCT No.: PCT/US2020/014448
§ 371 (c)(1),
(2) Date: Jun. 3, 2022

(87) PCT Pub. No.: WO2021/150212
PCT Pub. Date: Jul. 29, 2021

(65) Prior Publication Data
US 2023/0001412 A1    Jan. 5, 2023

(51) Int. Cl.
*B01L 3/00*        (2006.01)
*B01L 7/00*        (2006.01)
(Continued)

(52) U.S. Cl.
CPC ........... *B01L 3/502715* (2013.01); *B01L 7/52* (2013.01); *C12Q 1/6844* (2013.01);
(Continued)

(58) Field of Classification Search
None
See application file for complete search history.

(56) References Cited

U.S. PATENT DOCUMENTS 6,448,064 B1    9/2002    Vo-Dinh et al.
2002/0137121 A1*  9/2002    Rubinsky ......... G01N 33/48728
435/29
(Continued)

FOREIGN PATENT DOCUMENTS

EP        1606416 A2    12/2005
WO    WO-2012058096        5/2012
WO        2020/222763 A1    11/2020

OTHER PUBLICATIONS

John Canals et al., "A point-of-care device for molecular diagnosis based in CMOS SPAD detectors with integrated Microfluidics", Sensors 2019, 19, 445.

*Primary Examiner* — Michael A Marcheschi
*Assistant Examiner* — Ashley Lopezlira
(74) *Attorney, Agent, or Firm* — Foley & Lardner LLP

(57)        ABSTRACT

A microfluidic reaction chamber with a reaction chamber circuit includes a microfluidic reaction chamber to contain a reaction fluid for amplification of nucleic acids, and a reaction chamber circuit disposed within the microfluidic reaction chamber. The microfluidic reaction chamber includes a base wall, a top wall parallel to the base wall and defined in part by a transparent lid, a first side wall, and a second side wall. The reaction chamber circuit is disposed within the microfluidic reaction chamber, and includes a top surface, a bottom surface, a first side wall, and a second side wall. The reaction chamber circuit is in fluidic contact with the reaction fluid and includes a photodetector to detect a fluorescence signal from a labeled fluorescent tag in the reaction fluid.

5 Claims, 15 Drawing Sheets

(51) Int. Cl.
    *C12Q 1/6844*      (2018.01)
    *G01N 21/64*       (2006.01)

(52) U.S. Cl.
    CPC ...... *G01N 21/6428* (2013.01); *B01L 2200/16*
        (2013.01); *B01L 2300/0645* (2013.01); *B01L*
             *2300/0654* (2013.01); *B01L 2300/12*
        (2013.01); *B01L 2300/18* (2013.01); *G01N*
                    *2021/6439* (2013.01)

(56)              References Cited

U.S. PATENT DOCUMENTS

| | | |
|---|---|---|
| 2005/0123947 A1 | 6/2005 | Quake et al. |
| 2008/0300146 A1 | 12/2008 | Ponjee et al. |
| 2009/0013768 A1 | 1/2009 | Pouteau et al. |
| 2011/0312745 A1 | 12/2011 | Silverbrook et al. |
| 2016/0356715 A1 | 12/2016 | Zhong et al. |
| 2019/0250102 A1 | 8/2019 | Iizuka et al. |
| 2019/0329254 A1 | 10/2019 | Oleksandrov et al. |

\* cited by examiner

700

116

114

101

MICROFLUIDIC REACTION CHAMBER WITH A REACTION CHAMBER CIRCUIT

CROSS-REFERENCE TO RELATED APPLICATIONS

This application is a U.S. National Stage filing under 35 U.S.C. § 371 of PCT Application No. PCT/US2020/014448, filed Jan. 21, 2020, incorporated by reference herein.

BACKGROUND

Microfluidics is a technology that applies across a variety of disciplines including engineering, physics, chemistry, microtechnology and biotechnology. Microfluidics involves the study of small volumes of fluid and how to manipulate, control and use such small volumes of fluid in various microfluidic systems and devices such as microfluidic chips. For example, microfluidic biochips (referred to as "lab-on-chip") are used in the field of molecular biology to integrate assay operations for purposes such as analyzing enzymes and nucleic acids, detecting biochemical toxins and pathogens, diagnosing diseases, etc.

Polymerase chain reaction (PCR) is a powerful tool in the field of molecular biology. This technique allows for replicating/amplifying trace amounts of nucleic acid fragments into quantities that may be analyzed in a meaningful way.

DETAILED DESCRIPTION

Figure 1:
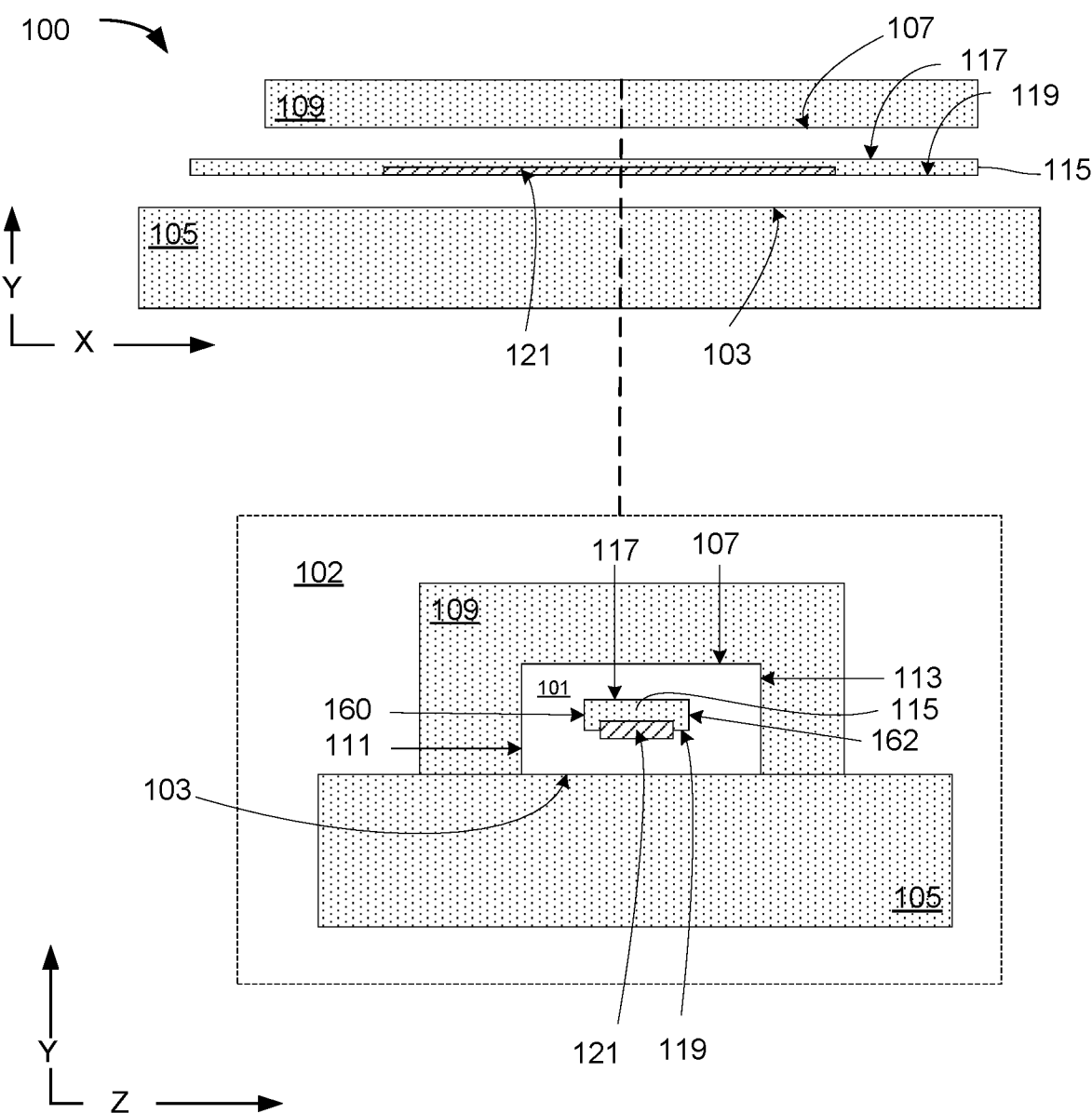
FIG. 1 is a schematic diagram of an example microfluidic reaction chamber with a reaction chamber circuit, according to the present disclosure.

In the following detailed description, reference is made to the accompanying drawings which form a part hereof, and in which is shown by way of illustration specific examples in which the disclosure may be practiced. It is to be understood that other examples may be utilized, and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

PCR is a method used in molecular biology to make many copies of a nucleic acid segment. Using PCR, a single copy (or more) of a nucleic acid sequence is exponentially amplified to generate thousands to millions or more copies of that particular nucleic acid segment. PCR is a temperature-mediated process involving cycling a reaction volume, or mixture, between set temperatures. Many PCR methods utilize the visible range of fluorescent spectroscopy to detect nucleic acids. With fluorescent spectroscopy, a fluorescence signal is detected from a labeled fluorescent tag after washing the unconjugated tag. Upon excitation from an external light source, these fluorescent labels emit a signal. A transducer, such as a photodetector, can collect these signals and transduce them to the electrical domain (i.e., voltage or current) for signal amplification and conditioning.

Detection mechanisms for fluorescent amplification utilize multiple devices. For instance, many fluorescence detection systems include an excitation light source, a fluorophore, wavelength filters to isolate emission photons from excitation photons, and a detector that registers emission photons and produces a recordable output, usually as an electrical signal. Moreover, depending on the fluorescent markers used, different respective optical filters may be used. The use of these multiple devices increases the cost and time of performing nucleic acid amplification and detection. In microfluidic devices which perform PCR in a portable handheld device, difficulty may arise in orienting circuitry for heating reaction fluids, and detecting fluorescent signals, in such a position that high throughput PCR may be performed without local overheating of the reaction volume of the PCR device and without incorporating external devices. Fluorescent labels, when attached directly to a probe molecule, allow for almost instantaneous detection. Fluorescence analysis is very sensitive, especially when special optical detection equipment is used. However, while sensitive optical detection equipment is available, it is rather expensive and thus out of reach for many researchers. Additionally, for each fluorescent probe used, when performing PCR or any other analytical technique involving microfluidic devices, a different respective light source and associated filter(s) may be used to detect the fluorescent signal. The present disclosure relates to an apparatus comprising a microfluidic reaction chamber to contain a reaction fluid for amplification of nucleic acids, and a reaction chamber circuit disposed within the microfluidic reaction chamber. The apparatus and method described herein may include the use of multiple filters and may therefore allow for multiple fluorescent probes to be used with a single handheld device. This reduces the use of multiple reaction chambers for multiple fluorescent probes (e.g., enabling multiplexing), and provides an integrated device for performing PCR and fluorescent detection. Moreover, the positioning of the reaction chamber circuit in the apparatus described herein, provides for high thermal efficiency, which permits the rapid and specific temperature changes for PCR to be achieved within the apparatus.

The present disclosure relates to an apparatus comprising a microfluidic reaction chamber to contain a reaction fluid for amplification of nucleic acids, and a reaction chamber circuit disposed within the microfluidic reaction chamber. In various examples, the microfluidic reaction chamber includes a base wall defined in part by a substrate, a top wall parallel to the base wall and defined in part by a transparent lid, a first side wall perpendicular to the base wall and defined in part by the transparent lid, and a second side wall perpendicular to the base wall and defined in part by the transparent lid. The reaction chamber circuit is disposed within the microfluidic reaction chamber, and includes a top surface parallel to and proximal to the top wall of the microfluidic reaction chamber, a bottom surface parallel to and distal to the top wall of the microfluidic reaction chamber, a first side wall parallel to the first side wall of the microfluidic reaction chamber, and a second side wall parallel to the second side wall of the microfluidic reaction chamber. As described herein, the top surface of the reaction chamber circuit, the bottom surface of the reaction chamber circuit, the first side wall of the reaction chamber circuit and the second side wall of the reaction chamber circuit are in fluidic contact with the reaction fluid. Moreover, the bottom surface of the reaction chamber circuit includes a photodetector to detect a fluorescence signal from a labeled fluorescent tag in the reaction fluid.

In additional examples, the apparatus includes a substrate, a transparent lid, and a reaction chamber circuit. The substrate includes a proximal end and a distal end opposite the proximal end, a first fluid channel traversing a width of the substrate, a second fluid channel traversing a width of the substrate, and a base wall disposed between the first fluid channel and the second fluid input/output. The transparent lid is coupled to the proximal end of the substrate and the distal end of the substrate to form a microfluidic reaction chamber. The reaction chamber circuit extends from the proximal end of the substrate to the distal end of the substrate and includes a top surface proximal to the transparent lid and a bottom surface distal to the transparent lid. The bottom surface of the reaction chamber circuit includes a photodetector to detect a fluorescence signal from a labeled fluorescent tag in a reaction fluid within the microfluidic reaction chamber.

In yet another example, a method includes receiving a reaction fluid via a first fluid channel of a microfluidic reaction chamber, the reaction fluid including a reagent and a biologic sample for amplification of nucleic acids included in the biologic sample. The method includes containing the reaction fluid in the microfluidic reaction chamber such that a reaction chamber circuit suspended within the microfluidic reaction chamber is in direct fluidic contact with the reaction fluid. Moreover, the method includes heating the reaction fluid to specified temperatures for nucleic acid amplification, and detecting a fluorescence signal from a labeled fluorescent tag in the reaction fluid indicative of amplification of the nucleic acids in the biologic sample, via a photodetector disposed on a bottom surface of the reaction chamber circuit and facing a base wall of the microfluidic reaction chamber.

Turning now to the figures, FIG. 1 is a schematic diagram of an example microfluidic reaction chamber with a reaction chamber circuit, according to the present disclosure. Particularly, FIG. 1 illustrates an apparatus 100 comprising a microfluidic reaction chamber 101 to contain a reaction fluid for amplification of nucleic acids. The microfluidic reaction chamber 101 may contain a small amount of reaction fluid, such as less than 10 uL of the reaction fluid. As used herein, a reaction fluid refers to or includes a fluid including components to perform nucleic acid amplification with fluorescence detection. The components in the reaction fluid may include, a biologic sample that contains the target sequence(s) to be amplified, an enzyme that polymerizes new nucleic acid strands, two (or more) nucleic acid primers, deoxyribonucleotide triphosphates (dNTPs), a buffer solution providing a suitable chemical environment for amplification and optimum activity and stability of the polymerase, and a reporter molecule such as fluorophores. Examples of the polymerase enzyme include, but are not limited to, DNA polymerase such as Taq DNA polymerase, and reverse transcriptase. Examples of the buffer solution include components such as bivalent cations, including magnesium (Mg) or manganese (Mn) ions and monovalent cations, such as potassium (K) ions, among others.

As illustrated in FIG. 1, a reaction chamber circuit 115 is disposed within the microfluidic reaction chamber 101. As used herein, a reaction chamber circuit refers to or includes circuitry to sense and measure properties of components of the reaction fluid in the microfluidic reaction chamber 101. In various examples, the reaction chamber circuit 115 includes a complimentary metal-oxide-semiconductor (CMOS) silicon circuit. Examples are not so limited, however, and in various examples the reaction chamber circuit 115 may include an n-type transistor, a p-type transistor, and/or a metal-oxide-semiconductor field-effect transistor (MOSFET), among others. The presence of a transistor type circuit in a microfluidic reaction chamber provides the ability to sense and measure properties of components of the fluid in the chamber. The reaction chamber circuit 115 can also be used to heat reaction fluid in the reaction chamber. The reaction fluid may be in contact with the reaction chamber circuit in order to sense and measure properties of components in the fluid and heat the fluid in the reaction chamber. These aspects enable an integrated-on-chip real time multiplex detection mechanism with increased heat efficiency and low power consumption and high speed due to faster thermal cycles for nucleic acid amplification and molecular diagnostics.

The microfluidic reaction chamber 101 is defined by several components. Referring to FIG. 1, the microfluidic reactor includes a base wall 103 defined in part by a substrate 105, and a top wall 107 parallel to the base wall 103 and defined in part by a transparent lid 109. A cross-section 102 of apparatus 100 along the Y axis further illustrates positioning of various components of apparatus 100. As illustrated in cross-section 102, the microfluidic reaction chamber 101 is further defined by a first side wall 111 perpendicular to the base wall 103 and defined in part by the transparent lid 109, and a second side wall 113 perpendicular to the base wall 103 and defined in part by the transparent lid 109. The transparent lid 109 may therefore partially form or make up the microfluidic reaction chamber 101 and may be mounted on or attached to the substrate 105.

The transparent lid 109 may comprise glass, quartz, poly (methyl methacrylate), polycarbonates, cyclic olefin copolymer, polyethylene terephthalate, polyethylene terephthalate glycol, and polyvinyl chloride for example, although other suitable materials are also contemplated. The substrate 105 may, for example, comprise a silicon-based wafer or may be formed of single crystalline silicon, polycrystalline silicon, gallium arsenide, glass, silica, ceramics, plastics, or a semiconducting material, for example. In some examples, the substrate 105 may be a composite material, and/or include multiple layers of different materials. While examples herein describe a microfluidic reaction chamber 101 defined in part by the substrate, in various examples the side walls and base wall of the microfluidic reaction chamber 101 may be defined entirely by the substrate, and the top wall may be defined in part or entirely by the transparent lid 109.

While the orientation of sides of the microfluidic reaction chamber 101 are described as being perpendicular to one another, such language is used to generally describe the position of one surface relative to another and does not imply a value of an angle. For instance, the first side wall 111 may be at an angle less than, greater than, or equal to ninety-degrees relative to the base wall 103. Similarly, second side wall 113 may be at an angle less than, greater than, or equal to ninety-degrees relative to the base wall 103. While the language "perpendicular to" is used throughout, such nomenclature is intended to describe a general orientation of one object relative to another such that the two objects intersect at an angle and does not describe the angle of orientation of the two objects unless otherwise mentioned. While the microfluidic reaction chamber 101 is illustrated as having a generally rectangular cross section (e.g., cross-section 102), examples are not so limited. The microfluidic reaction chamber 101 may have a square, rhomboid, or parallelogram shaped cross-section, or have curved or compound sides.

A reaction chamber circuit 115 is disposed within the microfluidic reaction chamber 101. In various examples, the reaction chamber circuit 115 is disposed within the microfluidic reaction chamber 101 such that the sides of the reaction chamber circuit 115 are in fluidic contact with the reaction fluid within the microfluidic reaction chamber 101. Accordingly, in various examples the reaction chamber circuit 115 includes a top surface 117 parallel to and proximal to the top wall 107 of the microfluidic reaction chamber 101, a bottom surface 119 parallel to and distal to the top wall 107 of the microfluidic reaction chamber 101, a first side wall 160 parallel to the first side wall 111 of the microfluidic reaction chamber 101, and a second side wall 162 parallel to the second side wall 113 of the microfluidic reaction chamber 101. The reaction chamber circuit 115 is suspended within the microfluidic reaction chamber 101 such that the top surface 117 of reaction chamber circuit 115, the bottom surface 119 of the reaction chamber circuit 115, the first side wall 160 of the reaction chamber circuit 115 and the second side wall 162 of the reaction chamber circuit 115 are in fluidic contact with the reaction fluid.

In various examples, detection of amplified nucleic acids is enabled by an integrated photosensor, such as a photodiode, avalanche photodiode (APD) or any other photosensitive element placed on the flipped side of a suspended portion of the reaction chamber circuit 115. This configuration helps to attenuate excitation light and prevents an integrated optical filter from being disposed on top of the photodetector, thereby drastically decreasing complexity and cost of the apparatus 100. For instance, in various examples the bottom surface 119 (or "flipped side") of the reaction chamber circuit 115 includes a photodetector 121 to detect a fluorescence signal from a labeled fluorescent tag in the reaction fluid, as discussed further herein.

Figure 2:
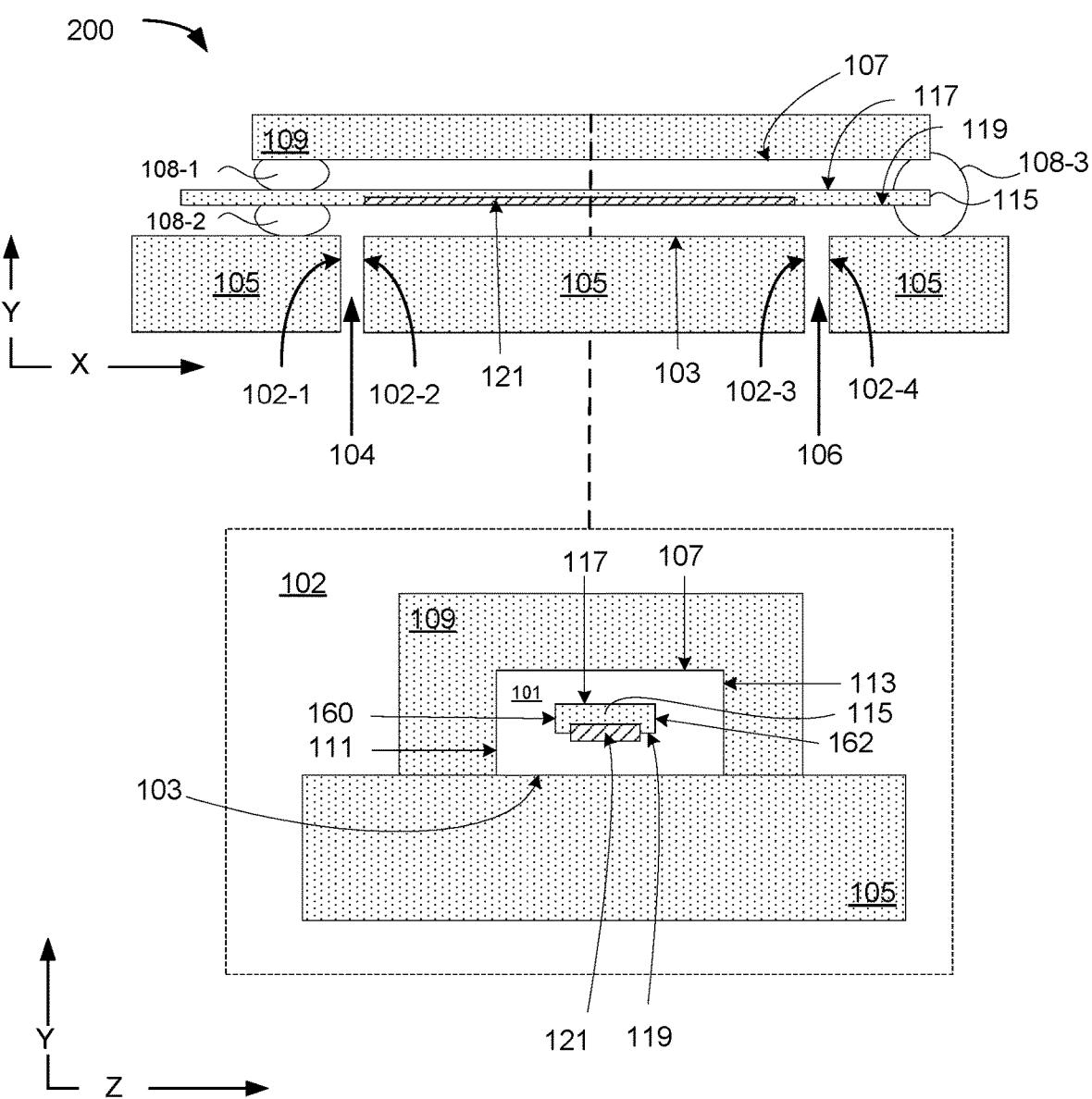
FIG. 2 is a schematic diagram of an example microfluidic reaction chamber with a reaction chamber circuit and including fluid channels, according to the present disclosure.

FIG. 2 is a schematic diagram of an example microfluidic reaction chamber with a reaction chamber circuit and including fluid channels, according to the present disclosure. The description of the parts or components of apparatus 100 above applies to corresponding parts in apparatus 200. As illustrated in FIG. 2, the apparatus 200 may include fluid channels 104 and 106 that allow the reaction fluid to flow in and/or out of the microfluidic reaction chamber 101. The fluid channels 104 and 106 may be defined by side walls of the substrate. For instance, side walls 102-1, 102-2, 102-3, and 102-4 of the substrate 105 form fluid channels 104, 106. Fluid channel 104 and fluid channel 106 each extend a width of the substrate 105, such that fluid may flow between the microfluidic reaction chamber 101 and the environment outside of apparatus 200.

The transparent lid 109 and the substrate 105 may, together, form the microfluidic reaction chamber 101. Referring to the cross-section 102, the first side wall 111 of the microfluidic reaction chamber 101 is defined in part by the transparent lid 109 and in part by the substrate 105. Similarly, the second side wall 113 is defined in part by the transparent lid 109 and in part by the substrate 105.

The ends of the microfluidic reaction chamber 101 may be plugged with end caps. For instance, the opening between the transparent lid 109 and the substrate 105 and/or the reaction chamber circuit 115 may be plugged with end caps 108-1, 108-2, and 108-3. The end caps 108-1, 108-2, and 108-3 shown may comprise a sealing adhesive or any other suitable adhesive.

Figure 3:
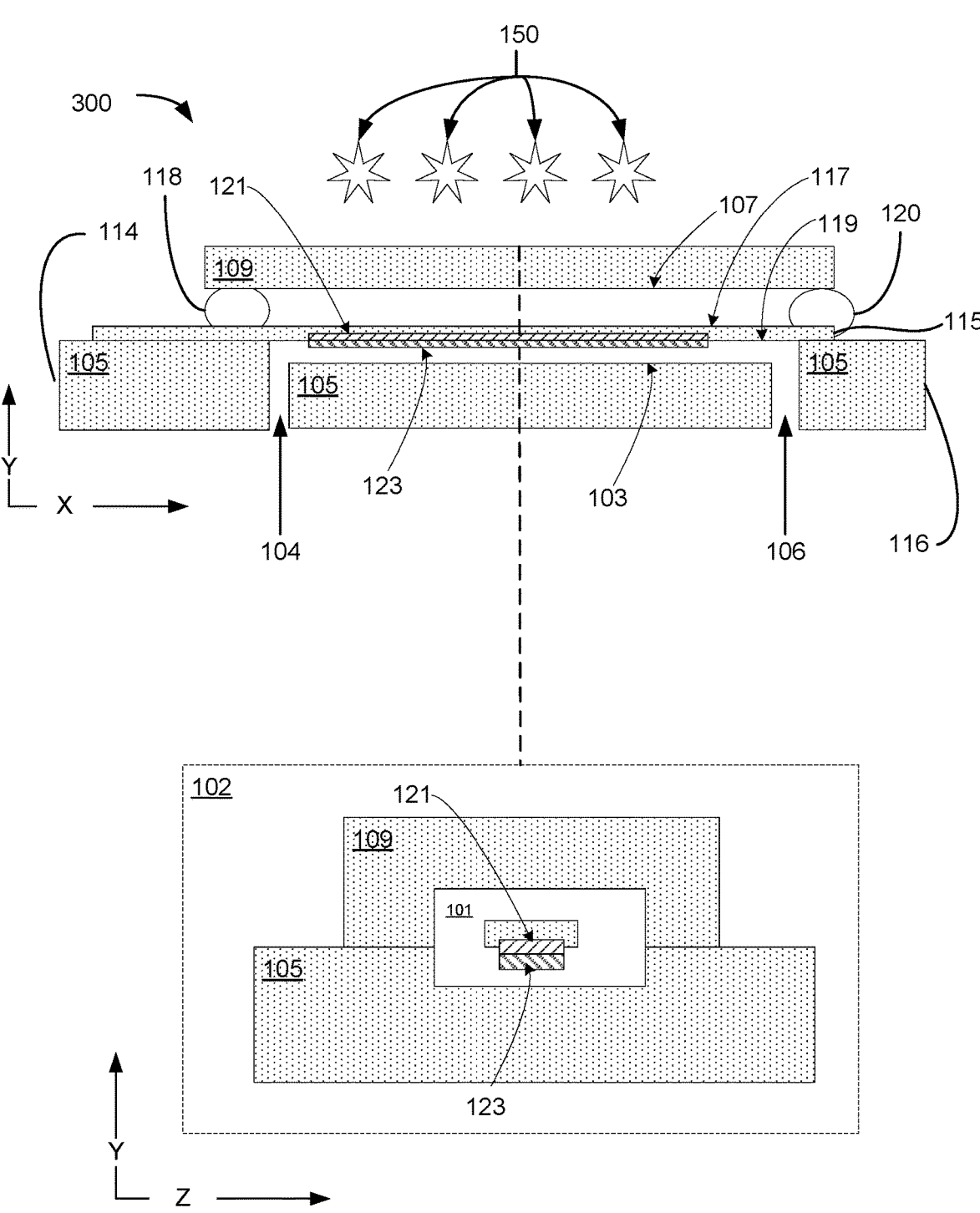
FIG. 3 is a schematic diagram of an example microfluidic reaction chamber with a reaction chamber circuit and including a filter, according to the present disclosure.

FIG. 3 is a schematic diagram of an example microfluidic reaction chamber with a reaction chamber circuit and including a filter, according to the present disclosure. The description of the parts or components of apparatus 100 above applies to corresponding parts in apparatus 300. Similar to FIG. 1, the example of FIG. 3 illustrates an apparatus 300 comprising a substrate 105 including a proximal end 114 and a distal end 116 opposite the proximal end 114, a first fluid channel 104 traversing a width of the substrate 105, a second fluid channel 106 traversing a width of the substrate 105, and a base wall 103 disposed between the first fluid channel 104 and the second fluid channel 106. The apparatus 300 further includes a transparent lid 109 coupled to the proximal end 114 of the substrate 105 and the distal end 116 of the substrate 105 to form a microfluidic reaction chamber 101.

The apparatus 300 includes a reaction chamber circuit 115 extending from the proximal end 114 of the substrate 105 to the distal end 116 of the substrate 105. The reaction chamber circuit 115 includes a top surface 117 proximal to the transparent lid 109 and a bottom surface 119 distal to the transparent lid 109.

The microfluidic reaction chamber 101 includes circuitry to heat the reaction fluid, the reaction fluid including a reagent and a biologic sample for amplification of nucleic acids included in the biologic sample. Accordingly, PCR or other nucleic acid amplification techniques may be performed with the apparatus 300, and the result of amplification may be detected by the apparatus 300 itself. In various examples, the reaction chamber circuit 115 includes a bottom surface 119 including a photodetector 121 to detect a fluorescence signal from a labeled fluorescent tag in a reaction fluid within the microfluidic reaction chamber 101. Excitation light source(s) 150 may be placed on the face side of the transparent lid 109, opposite of the top wall 107.

As illustrated in FIG. 3, the base wall 103 of the substrate 105 between the first fluid channel 104 and the second fluid channel 106 is recessed relative to a surface of the proximal end 114 and a surface of the distal end 116. The reaction chamber circuit 115 is coupled to the surface of the proximal end 114 of the substrate 105 and the surface of the distal end 116 of the substrate 105. As such, the recessed portion of the substrate 105 in combination with the first fluid channel 104 and the second fluid channel 106 allow for the movement of the reaction fluid in and/or out of the microfluidic reaction chamber 101.

In the example illustrated in FIG. 3, the transparent lid 109 is coupled to the reaction chamber circuit 115 via an adhesive end cap 118 disposed at the proximal end 114 of the substrate 105 and an adhesive end cap 120 disposed at the distal end 116 of the substrate 105. The adhesive end cap 118 may comprise the same or different material than the adhesive end cap 120.

To avoid direct illumination of the photodetector 121 from the excitation light, the photodetector 121 is placed on the bottom surface 119 of the reaction chamber circuit 115 and facing towards substrate 105. While FIG. 3 illustrates four excitation light sources, more or fewer light sources may be used. Moreover, excitation lights may be initiated sequentially to excite and detect presence of different fluorescent probes. The excitation lights may be a narrow band light sources or a plurality of different bandpass light sources illuminating the top of the transparent lid 109 to excite fluorescent markers within the microfluidic reaction chamber 101. This design enables an integrated-on-chip real time multiplex detection apparatus and increased heat efficiency with low power consumption for nucleic acid amplification and molecular diagnostics devices.

In various examples, the reaction chamber circuit 115 further includes an optical filter 123 disposed on a surface of the photodetector 121 proximal to the substrate 105. The filter 123 blocks unwanted traces of excitation light. The filter 123 may be an emission filter that allows fluorescence from the reaction fluid in the microfluidic reaction chamber 101 to reach the photodetector 121 while blocking unwanted traces of excitation light. Filter 123 may allow a narrow band of wavelengths to pass through it, around the peak fluorophore emission wavelength. Incident radiation outside of the wavelength range is either partially or totally blocked by the filter 123. As illustrated in cross-section 102, the filter 123 may be disposed in direct congruent contact with the photodetector 121 on the bottom surface 119 of the reaction chamber circuit 115.

While not illustrated in FIG. 3, additional filters may be used in apparatus 300. For instance, an excitation filter or a plurality of excitation filters may be disposed between the excitation light sources 150 and the transparent lid 109. The excitation filter(s) may also allow a narrow band of wavelengths to pass through it, around the peak fluorophore excitation wavelength, and may reflect wavelengths around the emission wavelength.

Figure 4:
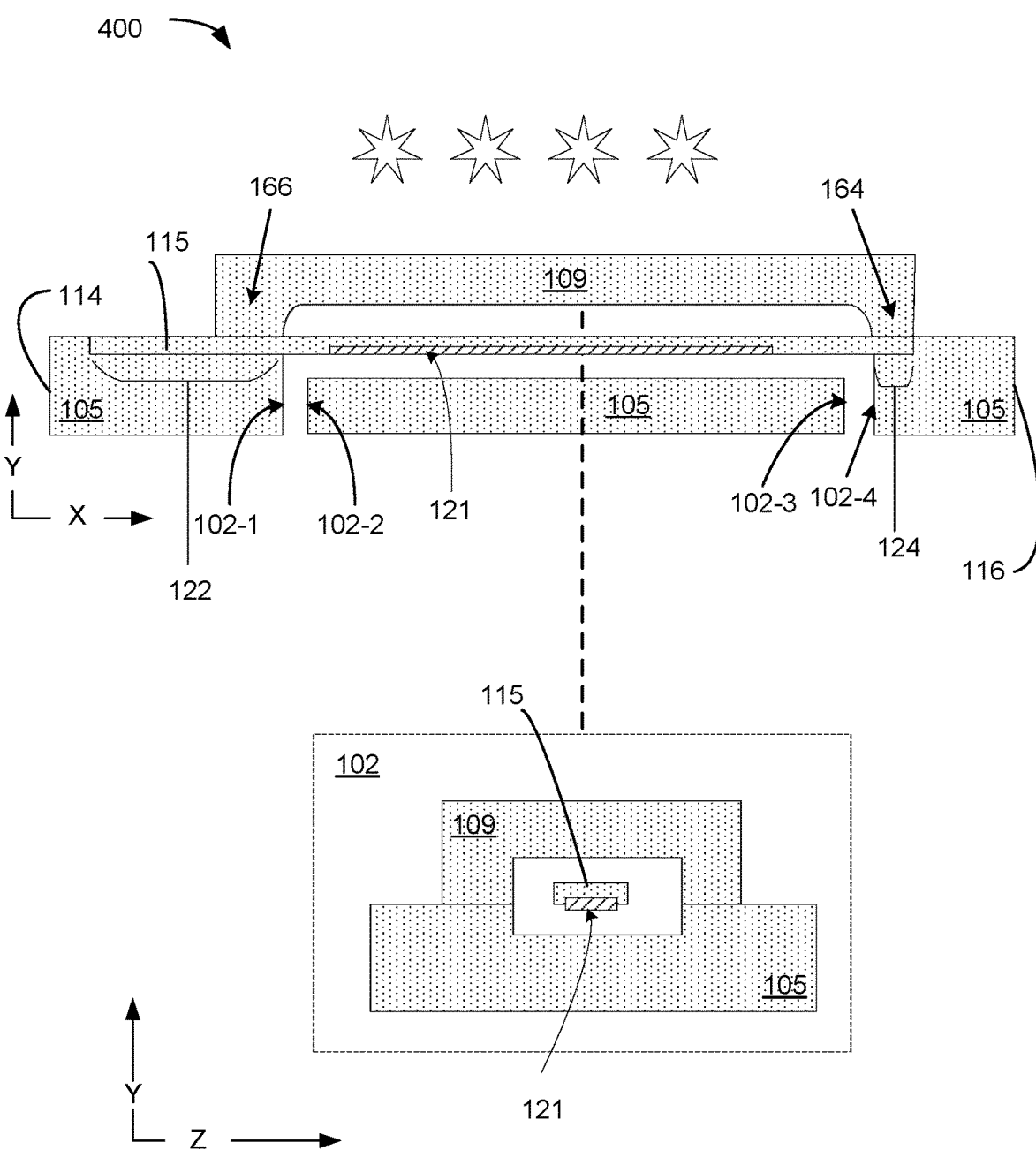
FIG. 4 is a schematic diagram of an example microfluidic reaction chamber with a reaction chamber circuit and recessed circuitry, according to the present disclosure.

FIG. 4 is a schematic diagram of an example microfluidic reaction chamber with a reaction chamber circuit and recessed circuitry, according to the present disclosure. The description of the parts or components of apparatus 100 above applies to corresponding parts in apparatus 400. In the example illustrated in FIG. 4, the substrate 105 includes a proximal end depression 122 at the proximal end 114 of the substrate 105 and a distal end depression 124 at the distal end 116 of the substrate 105, wherein the reaction chamber circuit 115 is disposed within the proximal end depression 122 and the distal end depression 124. The depth of the proximal end depression 122 is equal to the depth of the reaction chamber circuit 115, and the depth of the distal end depression 124 is equal to the depth of the reaction chamber circuit 115, such that the reaction chamber circuit 115 is relatively level with the substrate 105.

In the example illustrated in FIG. 4, side walls 102-1, 102-2, 102-3, and 102-4 of the substrate 105 form fluid channels 104, and 106. A base wall 103 of the microfluidic reaction chamber 101 between the fluid channels 104, 106 and proximal to the reaction chamber circuit 115 is recessed relative to a proximal end 114 of the substrate 105 and a distal end 116 of the substrate 105 to permit passage of the reaction fluid between the fluid channels 104, 106. The apparatus 400 is similar in construction to apparatus 300 illustrated in FIG. 3. However, the transparent lid 109 is coupled directly to the reaction chamber circuit 115, via side edges 164 and 166. As illustrated, the transparent lid 109 includes an enclosed cavity formed by the side edges 164 and 166 of the transparent lid 109.

Figure 5:
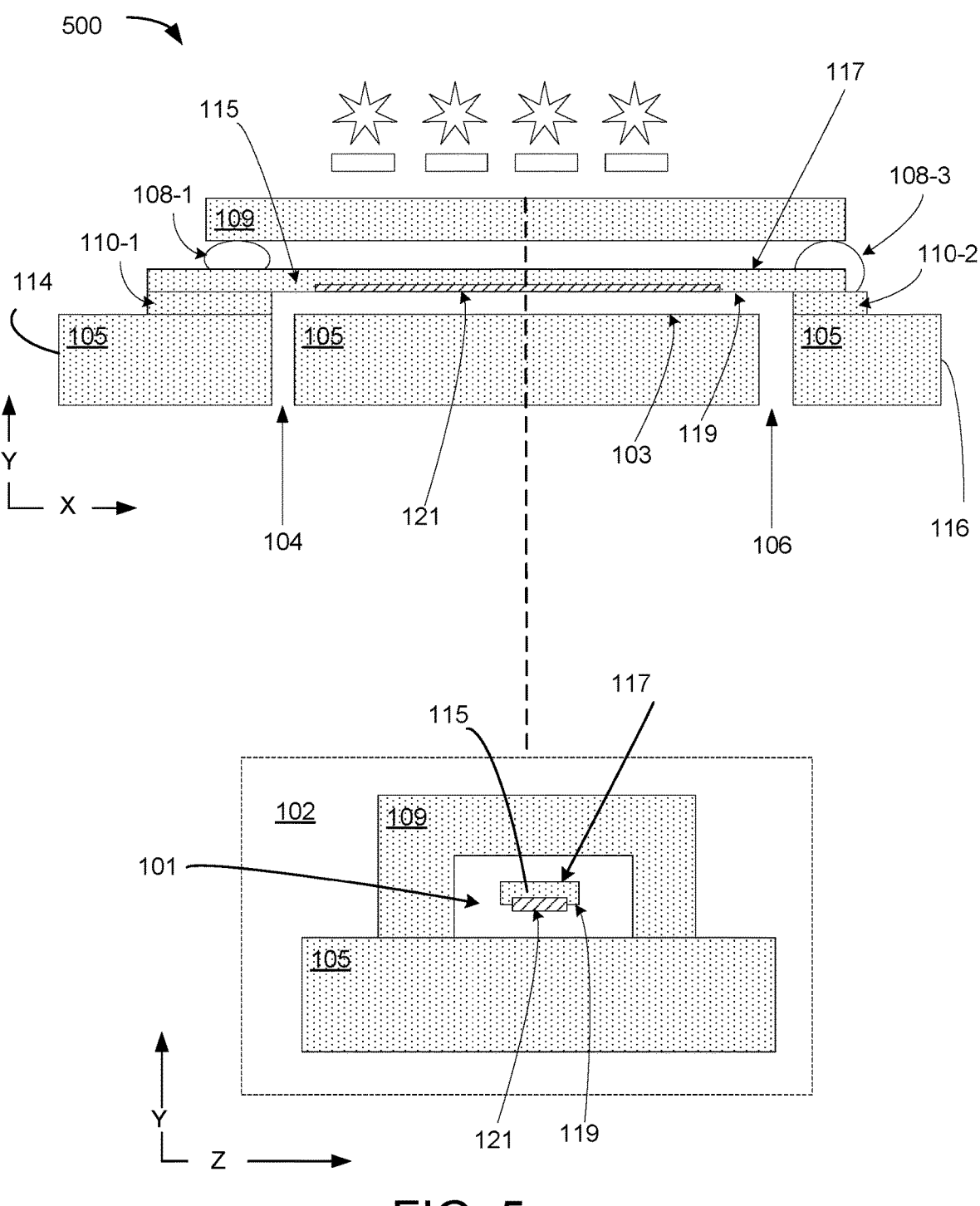
FIG. 5 is a schematic diagram of an example microfluidic reaction chamber with a reaction chamber circuit and suspension posts, according to the present disclosure.

FIG. 5 is a schematic diagram of an example microfluidic reaction chamber with a reaction chamber circuit and suspension posts, according to the present disclosure. The description of the parts or components of apparatus 100 above applies to corresponding parts in apparatus 500. In the example illustrated in FIG. 5, the substrate 105 is not recessed, rather, posts 110-1 and 110-2 support the reaction chamber circuit 115. Like FIG. 1, edges of the transparent lid 109 are plugged by adhesive end caps 108-1 and 108-3. The posts may be composed of silicon or other suitable material. The posts may be of a width ranging from about 50 µm thick to about 675 µm thick.

Figure 6:
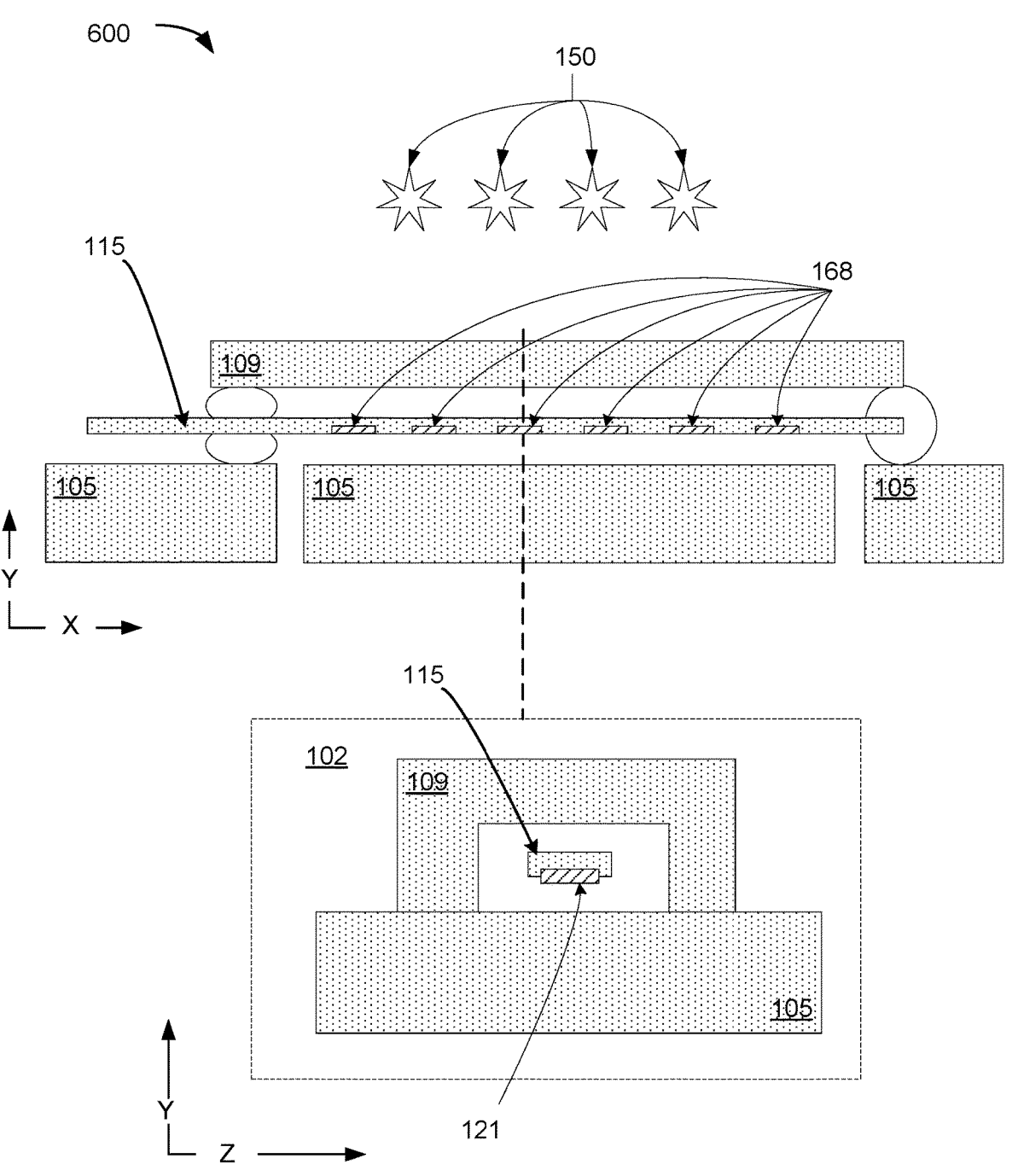
FIG. 6 is a schematic diagram of an example microfluidic reaction chamber with a reaction chamber circuit and an array of photodetectors, according to the present disclosure.

FIG. 6 is a schematic diagram of an example microfluidic reaction chamber with a reaction chamber circuit and an array of photodetectors, according to the present disclosure. The description of the parts or components of apparatus 100 above applies to corresponding parts in apparatus 600. In the example illustrated in FIG. 6, narrow band light sources 150 may operate sequentially to detect individual fluorescent probes enabling PCR multiplexing. In such examples, an array of photodetectors 168 may be arranged spatially along the reaction chamber circuit 115. Each photodetector of the array of photodetectors 168 may detect a different range of fluorescence, thereby enabling parallel detection of multiple fluorescent probes. The light sources 150 may be grouped to run sequentially or be ordered to minimize excitation of one probe by neighboring light sources.

Figure 7:
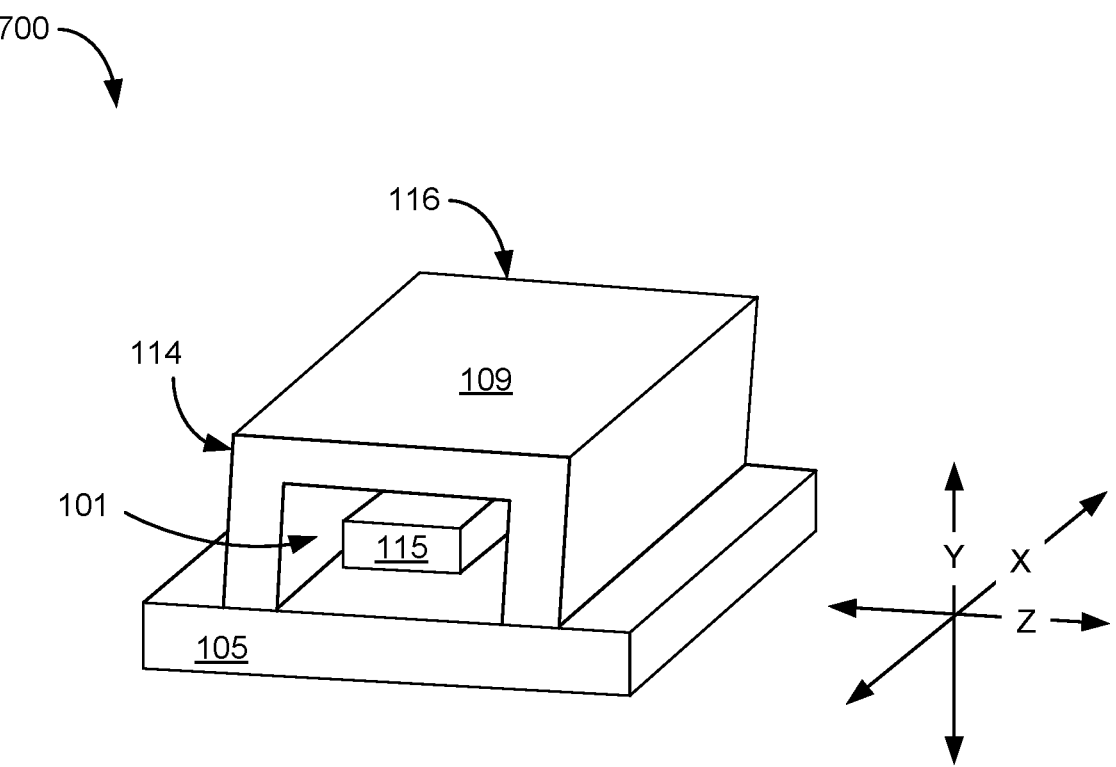
FIG. 7 is a multi-dimensional view of an example microfluidic reaction chamber with a reaction chamber circuit, according to the present disclosure.

FIG. 7 is a multi-dimensional view of an example microfluidic reaction chamber with a reaction chamber circuit, according to the present disclosure. The description of the parts or components of apparatus 100 above applies to corresponding parts in apparatus 700. Particularly, FIG. 7 illustrates an apparatus 700 comprising a microfluidic reaction chamber 101 to contain a reaction fluid, and a reaction chamber circuit 115 suspended within the microfluidic reaction chamber 101. As described herein, the reaction fluid includes a reagent and a biologic sample for amplification of nucleic acids included in the biologic sample. The microfluidic reaction chamber 101 includes a substrate 105 including a proximal end 114 and a distal end 116 opposite the proximal end 114, and a transparent lid 109 coupled to the substrate 105. As illustrated in FIG. 7, the reaction chamber circuit 115 is in direct fluidic contact with the reaction fluid, such that all four sides of the reaction chamber circuit 115 are in contact with the reaction fluid. The reaction chamber circuit 115 extends along the length of the apparatus 700 in the x plane, while fluid channels (not illustrated in FIG. 7)

allow for the passage of reaction fluid in and/or out of the microfluidic reaction chamber 101 in along the y plane.

Figure 8:
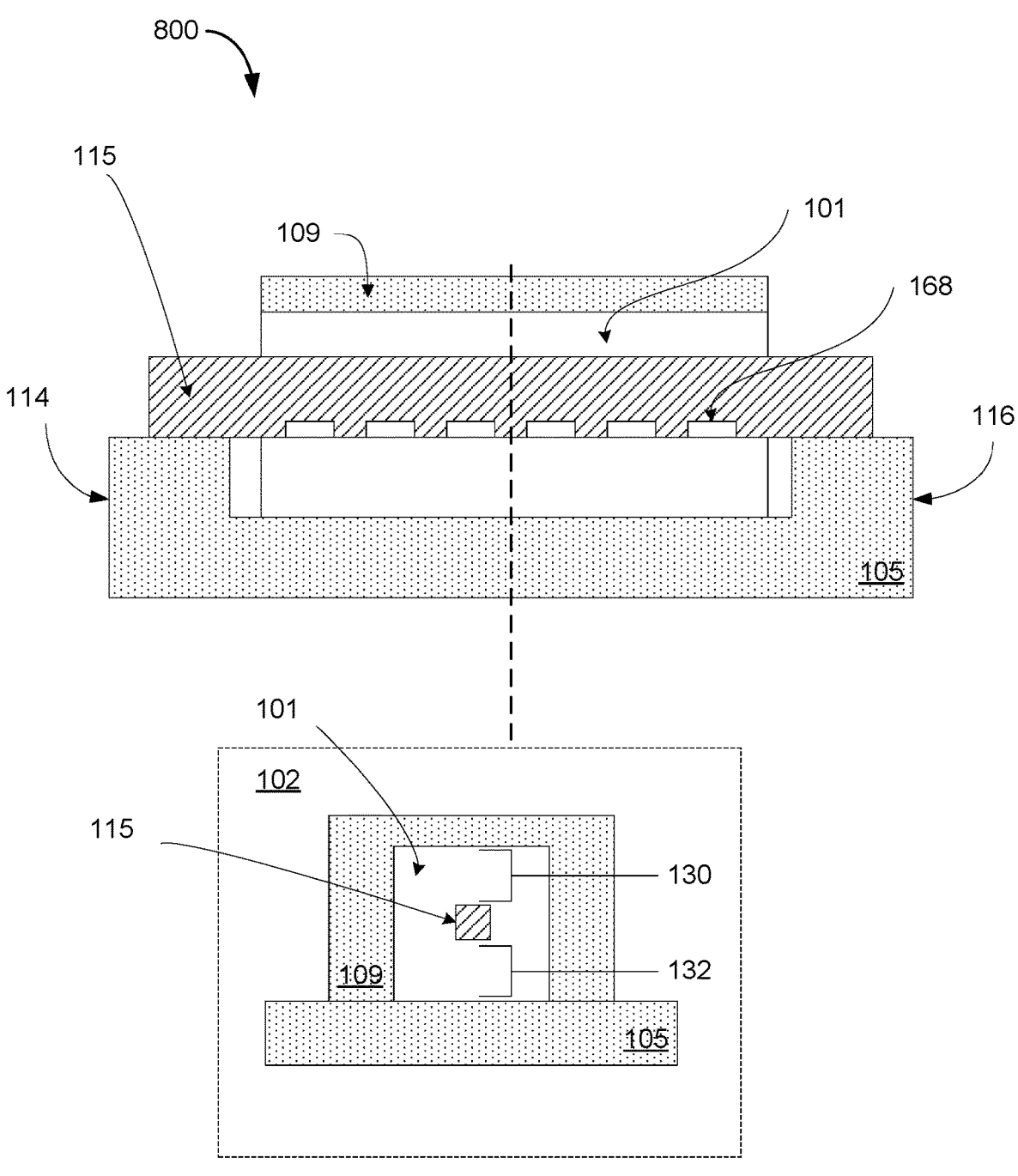
FIG. 8 is a schematic diagram of an example microfluidic reaction chamber with a reaction chamber circuit and open capillary ends, according to the present disclosure.

FIG. 8 is a schematic diagram of an example microfluidic reaction chamber with a reaction chamber circuit and open capillary ends, according to the present disclosure. The description of the parts or components of apparatus 100 above applies to corresponding parts in apparatus 800. Particularly, the example illustrated in FIG. 8 illustrates the reaction chamber circuit 115 suspended centrally in the microfluidic reaction chamber 101. As illustrated, the ends of the reaction chamber circuit 115, are in contact with the substrate surface 105. Reaction fluid surrounds the reaction chamber circuit 115 on all sides, such that the distance 130 between the reaction chamber circuit 115 and the transparent lid 109 on one side, is the same as the distance 132 between the reaction chamber circuit 115 and the substrate 105 on a second side. Reaction fluid may enter and/or exit the microfluidic reaction chamber 101 through open capillary ends on the proximal end 114 and the distal end 116. An array of photodetectors 168 disposed on the reaction chamber circuit 115 may face the substrate 105 as illustrated, or the transparent lid 109.

Figure 9:
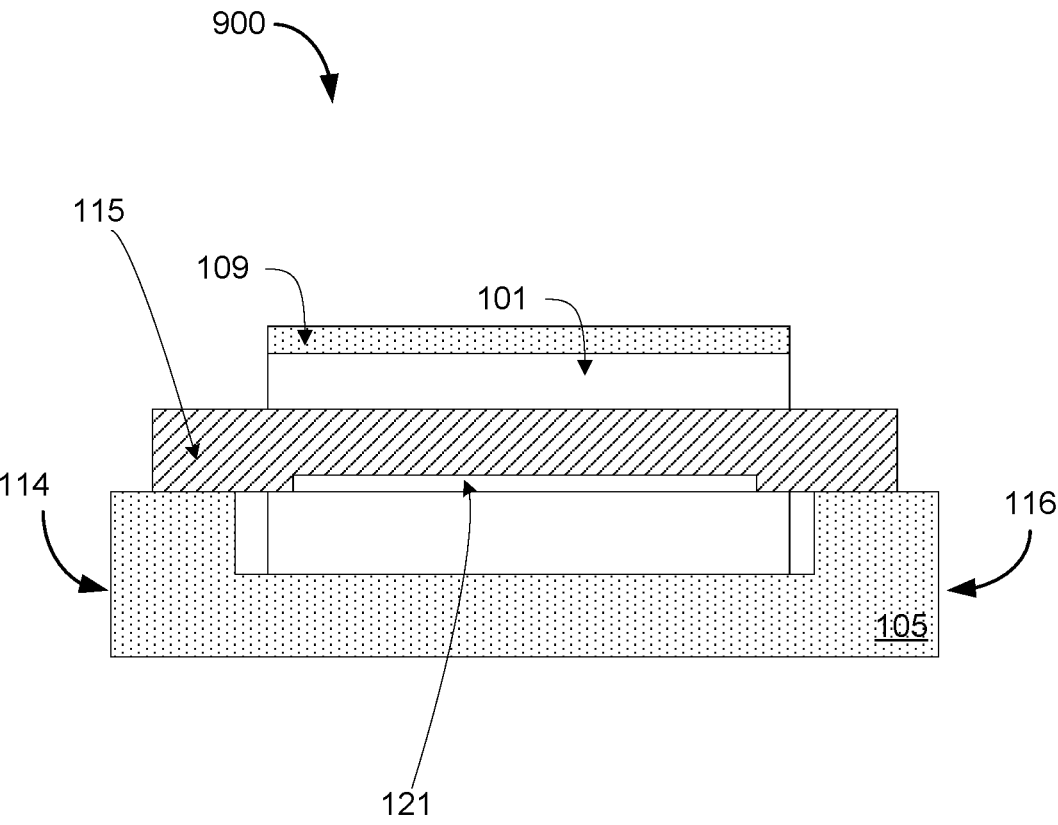
FIG. 9 is a schematic diagram of another example microfluidic reaction chamber with a reaction chamber circuit and open capillary ends, according to the present disclosure.

FIG. 9 is a schematic diagram of another example microfluidic reaction chamber with a reaction chamber circuit and open capillary ends, according to the present disclosure. The description of the parts or components of apparatus 100 above applies to corresponding parts in apparatus 900. Particularly, the example illustrated in FIG. 9 illustrates the reaction chamber circuit 115 suspended centrally in the microfluidic reaction chamber 101. As illustrated, the ends of the reaction chamber circuit 115, are in contact with the substrate surface 105. Reaction fluid may enter and/or exit the microfluidic reaction chamber 101 through open capillary ends on the proximal end 114 and the distal end 116. A photodetector 121 disposed on the reaction chamber circuit 115 may face the substrate 105 as illustrated, or the transparent lid 109.

Figure 10:
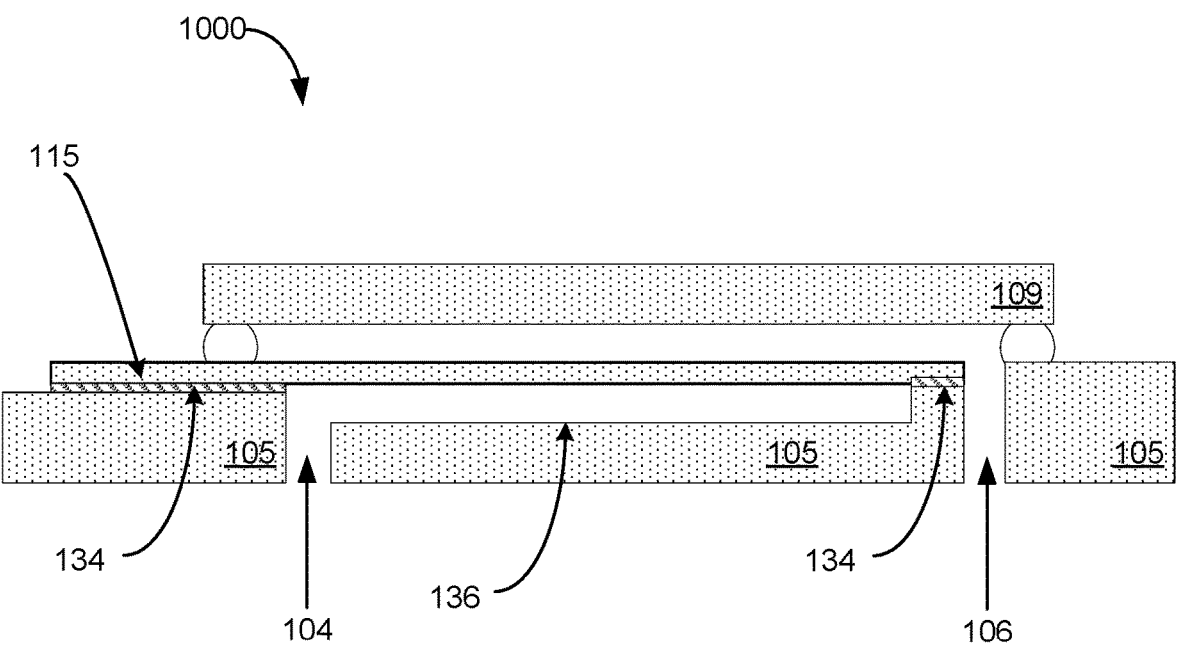
FIG. 10 is a schematic diagram of an example microfluidic reaction chamber with a reaction chamber circuit and a recessed substrate, according to the present disclosure.

FIG. 10 is a schematic diagram of an example microfluidic reaction chamber with a reaction chamber circuit and a recessed substrate, according to the present disclosure. The description of the parts or components of apparatus 100 above applies to corresponding parts in apparatus 1000. Particularly, the example of FIG. 10 illustrates a reaction chamber circuit 115 mounted on a substrate 105 with adhesive 134 at each end of the reaction chamber circuit 115. A relief 136 in the substrate 105 allows fluid to reach the bottom side of the reaction chamber circuit 115, and a transparent lid 109 is mounted over the reaction chamber circuit 115 onto the substrate 105. Fluid channels 104 and 106 may be created through the substrate 105 to allow reaction fluid to enter and exit the microfluidic reaction chamber 101.

Figure 11:
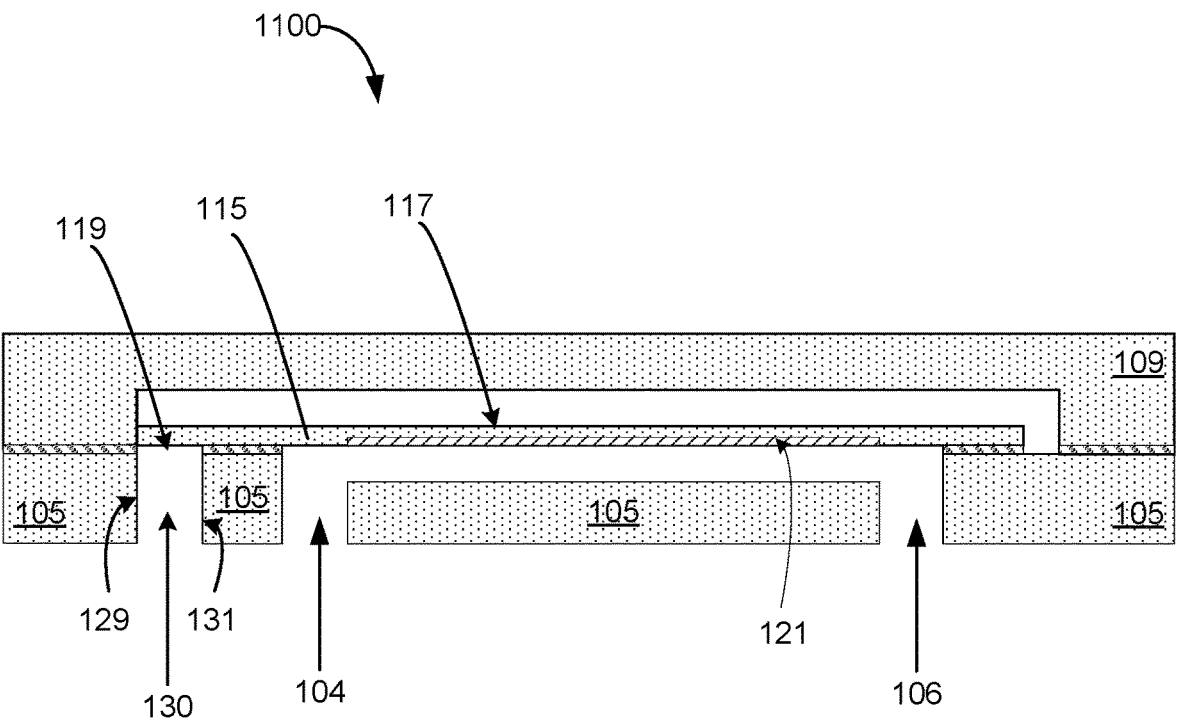
FIG. 11 is a schematic diagram of an example microfluidic reaction chamber with a reaction chamber circuit and sealing adhesive, according to the present disclosure.

FIG. 11 is a schematic diagram of an example microfluidic reaction chamber with a reaction chamber circuit and sealing adhesive, according to the present disclosure. The description of the parts or components of apparatus 100 above applies to corresponding parts in apparatus 1100. The reaction chamber circuit 115 includes circuitry to heat the reaction fluid to specified temperatures for nucleic acid amplification, and a photodetector 121 disposed on a bottom surface 119 of the reaction chamber circuit 115 and facing the substrate 105 of the microfluidic reaction chamber 101. As described herein, the bottom surface 119 of the reaction chamber circuit 115 is distal to the transparent lid 109 relative to a top surface 117 of the reaction chamber circuit 115. The photodetector 121 detects a fluorescence signal from a labeled fluorescent tag in the reaction fluid indicative of amplification of the nucleic acids in the biologic sample. Moreover, a first fluid channel 104 may traverse a width of the substrate 105, and a second fluid channel 106 may traverse the width of the substrate 105. The photodetector 121 may detect the fluorescence signal from the fluorescent tag responsive to excitation by narrow band light passing through the transparent lid 109 and scattered by the substrate 105.

The reaction chamber circuit 115 is oriented such that the circuitry faces the substrate 105. An aperture 130 is included such that electrical power and signal can reach the reaction chamber circuit 115 through the substrate 105. A relief in the substrate allows the reaction chamber circuit 115 to be in direct contact/access to the fluid in the chamber.

An aperture 130 traversing the width of the substrate 105, wherein side walls 129, 131 of the aperture 130 are defined by the substrate 105 and a top wall of the aperture is defined by the bottom surface 119 of the reaction chamber circuit 115, the aperture 130 to receive an electrical connection for the apparatus.

Figure 12:
FIG. 12 is a schematic diagram of an example microfluidic reaction chamber with a reaction chamber circuit and a heat pipe, according to the present disclosure.
Figure 12:
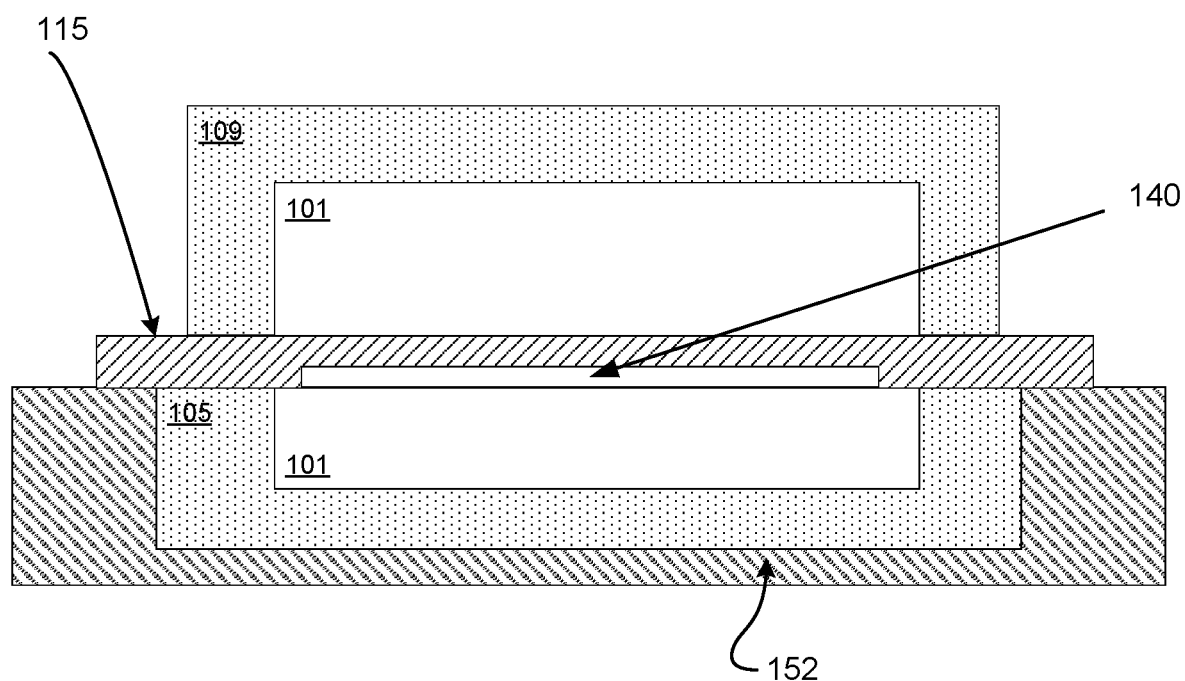

FIG. 12 is a schematic diagram of an example microfluidic reaction chamber with a reaction chamber circuit and a heat pipe, according to the present disclosure. The description of the parts or components of apparatus 100 above applies to corresponding parts in apparatus 1200. The heat pipe 152 may draw heat from the reaction chamber circuit 115 and from the substrate 105 to cool the microfluidic reaction chamber 101. The heat pipe 152 may extend around a surface of the substrate 105 and be in direct physical contact with both the substrate and the reaction chamber circuit 115, as illustrated.

Figure 13:
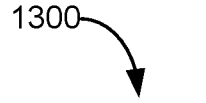
FIG. 13 is a schematic diagram of an example microfluidic reaction chamber with a displaced reaction chamber circuit, according to the present disclosure.
Figure 13:
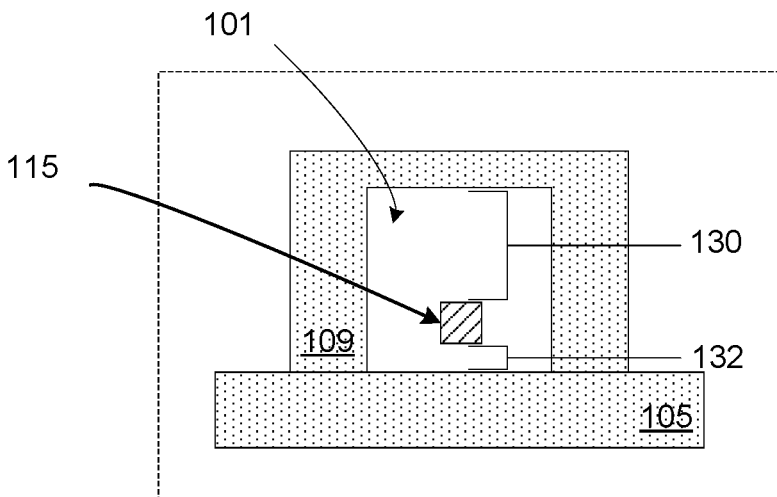

FIG. 13 is a schematic diagram of an example microfluidic reaction chamber with a displaced reaction chamber circuit, according to the present disclosure. The description of the parts or components of apparatus 100 above applies to corresponding parts in apparatus 1300. The reaction chamber circuit 115 including a top surface 117 opposite the bottom surface 119 and proximal to the transparent lid 109, and wherein the reaction chamber circuit 115 is disposed within the microfluidic reaction chamber 101 such that a distance 130 between the top surface 117 of the reaction chamber circuit 115 and the transparent lid 109 is greater than a distance 132 between the bottom surface 119 of the reaction chamber circuit 115 and the substrate 105.

Figure 14:
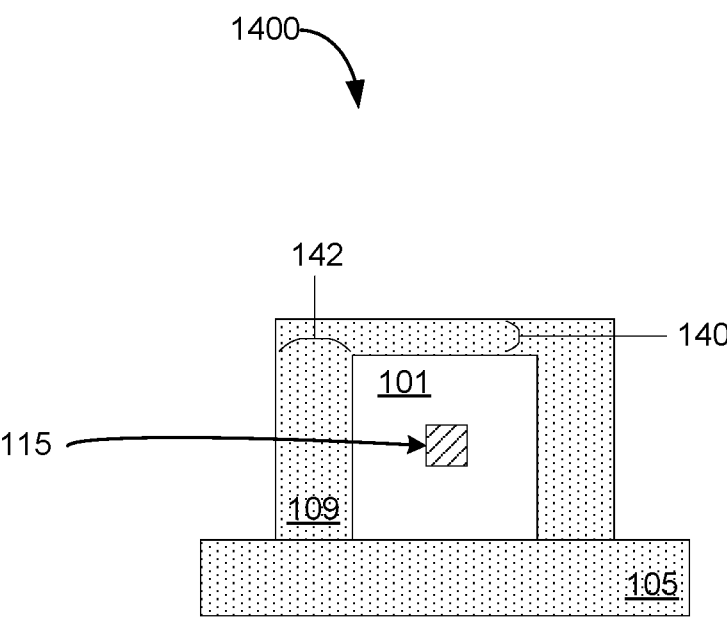
FIG. 14 is a schematic diagram of an example microfluidic reaction chamber with a reaction chamber circuit and reduced transparent lid, according to the present disclosure.

FIG. 14 is a schematic diagram of an example microfluidic reaction chamber with a reaction chamber circuit and reduced transparent lid, according to the present disclosure. Various methods may be used to cool the reaction chamber circuit 115, including use of a heat pipe as illustrated in regard to FIG. 12, and changing a distance between the reaction chamber circuit 115 and the substrate 105 as discussed in regards to FIG. 13. The description of the parts or components of apparatus 100 above applies to corresponding parts in apparatus 1400. FIG. 14 illustrates an additional method for cooling the reaction chamber circuit 115, by reducing a width of the transparent lid 109. For instance, the top width 140 of the transparent lid 109 may be less than the side width 142 of the transparent lid 109 so that heat may dissipate to the surrounding air.

Figure 15:
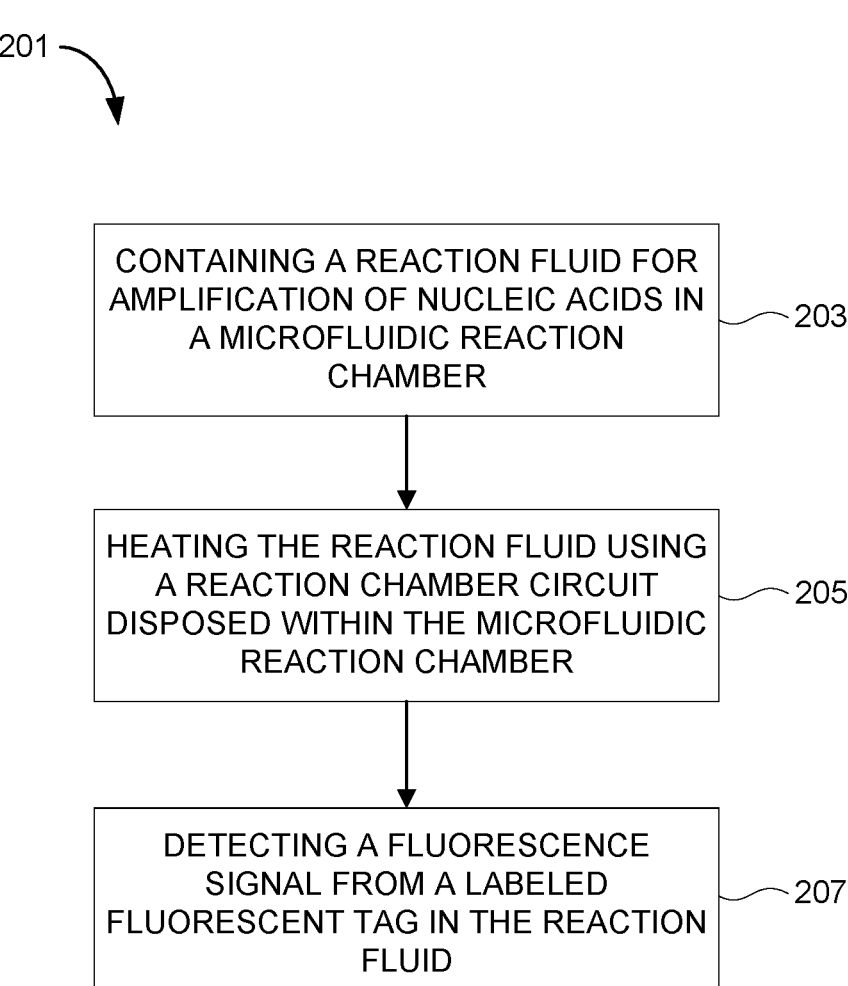
FIG. 15 is an example flow diagram of a method, according to the present disclosure.

FIG. 15 is an example flow diagram of a method 201, according to the present disclosure. At 203, the method 201 includes containing a reaction fluid for amplification of nucleic acids in a microfluidic reaction chamber. As discussed with regards to FIG. 1, the microfluidic reaction chamber includes a base wall defined in part by a substrate, a top wall parallel to the base wall and defined in part by a transparent lid, a first side wall perpendicular to the base wall and defined in part by the transparent lid, and a second side wall perpendicular to the base wall and defined in part by the transparent lid.

At 205, the method 201 includes heating the reaction fluid using a reaction chamber circuit disposed within the micro- fluidic reaction chamber. Again, referring to FIG. 1, the reaction chamber circuit includes a top surface parallel to and proximal to the top wall of the microfluidic reaction chamber, a bottom surface parallel to and distal to the top wall of the microfluidic reaction chamber, a first side wall parallel to the first side wall of the microfluidic reaction chamber, and a second side wall parallel to the second side wall of the microfluidic reaction chamber.

At 207, the method 203 includes detecting a fluorescence signal from a labeled fluorescent tag in the reaction fluid. The fluorescence signal is detected from a labeled fluores- cent tag in the reaction fluid indicative of amplification of the nucleic acids in the biologic sample, via a photodetector disposed on a bottom surface of the reaction chamber circuit and facing a substrate of the microfluidic reaction chamber. As described herein, the microfluidic reaction chamber includes a transparent lid. Accordingly, detecting the fluo- rescence signal at 207 may include detecting the fluores- cence signal from the fluorescent tag responsive to excita- tion by narrow band light passing through the transparent lid.

In various examples, detection of a plurality of fluorescent signals may be multiplexed, such that more than one fluo- rescent signal may be detected at a time and using a same apparatus. For instance, referring to FIG. 6, each of the excitation light sources 150 may provide light of a different wavelength in relation to the remainder of the excitation light sources 150. Similarly, each of the photoreactors in the array of photodetectors 168 may detect fluorescent signals associated with a different respective wavelength in relation to the remainder of the array of photodetectors 168. As such, detecting the fluorescence signal may include detecting a plurality of fluorescence signals from a plurality of fluores- cent tags responsive to excitation by a plurality of different light sources passing through the transparent lid.

In various examples, the plurality of light sources may be used in an ordered manner to minimize cross-excitation of photodetectors. For instance, detecting the fluorescence sig- nal may include exposing the reaction fluid to the different respective light sources (e.g., 150 illustrated in FIG. 6) in a sequential manner. Additionally, and/or alternatively, detect- ing the fluorescence signal may include exposing the reac- tion fluid to the different respective light sources in parallel, such that groups of the light sources are illuminated at a given time. Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. An apparatus comprising:
a microfluidic reaction chamber configured to contain a reaction fluid for amplification of nucleic acids, the microfluidic reaction chamber including a base wall defined in part by a substrate, a top wall parallel to the base wall and defined in part by a transparent lid, a first side wall perpendicular to the base wall and defined in part by the transparent lid, and a second side wall perpendicular to the base wall and defined in part by the transparent lid; and
a reaction chamber circuit disposed within the microflu- idic reaction chamber, the reaction chamber circuit including a top surface parallel to and proximal to the top wall of the microfluidic reaction chamber, a bottom surface parallel to and distal to the top wall of the microfluidic reaction chamber and separated from the base wall of the microfluidic reaction chamber to form a gap between the bottom surface of the reaction chamber circuit and the base wall of the microfluidic reaction chamber, a first side wall parallel to the first side wall of the microfluidic reaction chamber, and a second side wall parallel to the second side wall of the microfluidic reaction chamber;
wherein the top surface of the reaction chamber circuit, the bottom surface of the reaction chamber circuit, the first side wall of the reaction chamber circuit and the second side wall of the reaction chamber circuit are in fluidic contact with the reaction fluid, and the bottom surface of the reaction chamber circuit includes a photodetector separated from the base wall of the microfluidic reaction chamber by the gap and config- ured to detect a fluorescence signal from a labeled fluorescent tag in the reaction fluid.

2. The apparatus of claim 1, wherein the reaction chamber circuit includes a complimentary metal-oxide-semiconduc- tor (CMOS) silicon circuit with circuitry disposed on the bottom surface facing the substrate.

3. The apparatus of claim 1, wherein the reaction chamber circuit further includes an optical filter disposed on a surface of the photodetector proximal to the substrate.

4. The apparatus of claim 1, wherein the first side wall of the microfluidic reaction chamber is further defined in part by the transparent lid and in part by the substrate, and the second side wall of the microfluidic reaction chamber is further defined in part by the transparent lid and in part by the substrate.

5. The apparatus of claim 4, wherein side walls of the substrate form fluid channels and wherein a base wall of the microfluidic reaction chamber between the fluid channels and proximal to the reaction chamber circuit is recessed relative to a proximal end of the substrate and a distal end of the substrate to permit passage of the reaction fluid between the fluid channels.

* * * * *